US010369311B2

(12) United States Patent
Zachar

(10) Patent No.: US 10,369,311 B2
(45) Date of Patent: Aug. 6, 2019

(54) LARYNGEAL MASK CUFF

(71) Applicant: AIRWAY MEDIX S.A., Warsaw (PL)

(72) Inventor: Oron Zachar, Tel Aviv (IL)

(73) Assignee: AIRWAY MEDIX S.A., Warsaw (PL)

(*) Notice: Subject to any disclaimer, the term of this patent is extended or adjusted under 35 U.S.C. 154(b) by 0 days.

(21) Appl. No.: 15/878,993

(22) Filed: Jan. 24, 2018

(65) Prior Publication Data

US 2019/0160243 A1 May 30, 2019

Related U.S. Application Data

(60) Provisional application No. 62/592,020, filed on Nov. 29, 2017.

(51) Int. Cl.
*A61M 16/04* (2006.01)
*A61M 16/08* (2006.01)

(52) U.S. Cl.
CPC .... *A61M 16/0434* (2013.01); *A61M 16/0409* (2014.02); *A61M 16/0488* (2013.01); *A61M 16/0816* (2013.01)

(58) Field of Classification Search
None
See application file for complete search history.

(56) References Cited

U.S. PATENT DOCUMENTS

| | | | |
|---|---|---|---|
| 3,599,620 A | 8/1971 | Balin | |
| 4,119,101 A | 10/1978 | Igich | |
| 4,134,407 A | 1/1979 | Elam | |
| 5,007,919 A | 4/1991 | Silva et al. | |
| 5,255,670 A | 10/1993 | Lomholt | |
| 5,632,271 A | 5/1997 | Brain | |
| 6,439,232 B1 * | 8/2002 | Brain | A61M 16/04 128/200.26 |

(Continued)

FOREIGN PATENT DOCUMENTS

| | | |
|---|---|---|
| CN | 106823086 A | 6/2017 |
| EP | 0 922 465 A2 | 6/1999 |

(Continued)

OTHER PUBLICATIONS

Ambu, AuraOnce AuraStraight brochure, Feb. 2009, total 4 pages.

(Continued)

*Primary Examiner* — Rachel T Sippel
(74) *Attorney, Agent, or Firm* — Sughrue Mion, PLLC

(57) ABSTRACT

A laryngeal mask airway (LMA) device is provided, which includes an inflatable annular cuff, a backplate attached to the cuff, and an airway tube. The cuff, when disposed in free space, is characterized by a pressure-volume curve that represents the pressure in the cuff when inflated to different volumes of the cuff that include a low-pressure volume corresponding to a low pressure of 10 cm H2O. The pressure-volume curve includes (a) a local maximum pressure at a medium volume of the cuff between 1.25 and 2.4 times the low-pressure volume, wherein the local maximum pressure is between 15 and 120 cm H2O, and (b) respective high-volume medium pressures corresponding to all high volumes of the cuff that are between 2.5 and 3 times the low-pressure volume. Each of the high-volume medium pressures is between 15 cm H2O and 99% of the local maximum pressure. Other embodiments are also described.

30 Claims, 8 Drawing Sheets

(56) References Cited

U.S. PATENT DOCUMENTS

| | | |
|---|---|---|
| 7,305,985 B2 | 12/2007 | Brain |
| 8,783,256 B2 | 7/2014 | Brain |
| 2003/0037790 A1* | 2/2003 | Brain .................... A61M 16/04 128/207.14 |
| 2008/0078403 A1* | 4/2008 | Clayton ................. A61L 29/04 128/207.15 |
| 2009/0120445 A1 | 5/2009 | Chikashige |
| 2012/0145160 A1 | 6/2012 | Brain |
| 2015/0283343 A1 | 10/2015 | Schnell et al. |
| 2015/0290410 A1 | 10/2015 | Schnell et al. |
| 2016/0158040 A1* | 6/2016 | Zupkofska ............... A61F 2/82 623/23.7 |

FOREIGN PATENT DOCUMENTS

| | | |
|---|---|---|
| GB | 2324735 | 6/2001 |
| WO | 2008/038430 A1 | 4/2008 |
| WO | 2015/015233 A1 | 2/2015 |
| WO | 2017153988 | 9/2017 |
| WO | 2018045555 | 3/2018 |

OTHER PUBLICATIONS

Rokamp Kim et al, "Tracheal tube and laryngeal mask cuff pressure during anaesthesia—mandatory monitoring is in need", BMC Anesthesiology, Dec. 2010 (text only), total 10 pages.
Teleflex, Quick-Reference-Guide LMA, 2013, total 2 pages.
Teleflex, LMA Supreme brochure, Mar. 2014, Total 2 pages.
"Two-balloon experiment", Wikipedia, downloaded from https://en.wikipedia.org/wiki/Two-balloon_experiment on Jan. 22, 2018, total 4 pages.
Communication dated Jan. 14, 2019 issued by the United States Patent and Trademark Office in U.S. Appl. No. 16/160,668.
Notice of Allowance dated Mar. 4, 2019 issued by the United States Patent and Trademark Office in U.S. Appl. No. 16/160,668.
Communication dated Jul. 11, 2018 from the United States Patent and Trademark Office in counterpart U.S. Appl. No. 15/951,564.
Notice of Allowance issued in U.S. Appl. No. 15/951,564 dated Nov. 13, 2018.
An International Search Report and a Written Opinion both dated Feb. 22, 2019, which issued during the prosecution of Applicant's PCT/IL2018/051306.

* cited by examiner

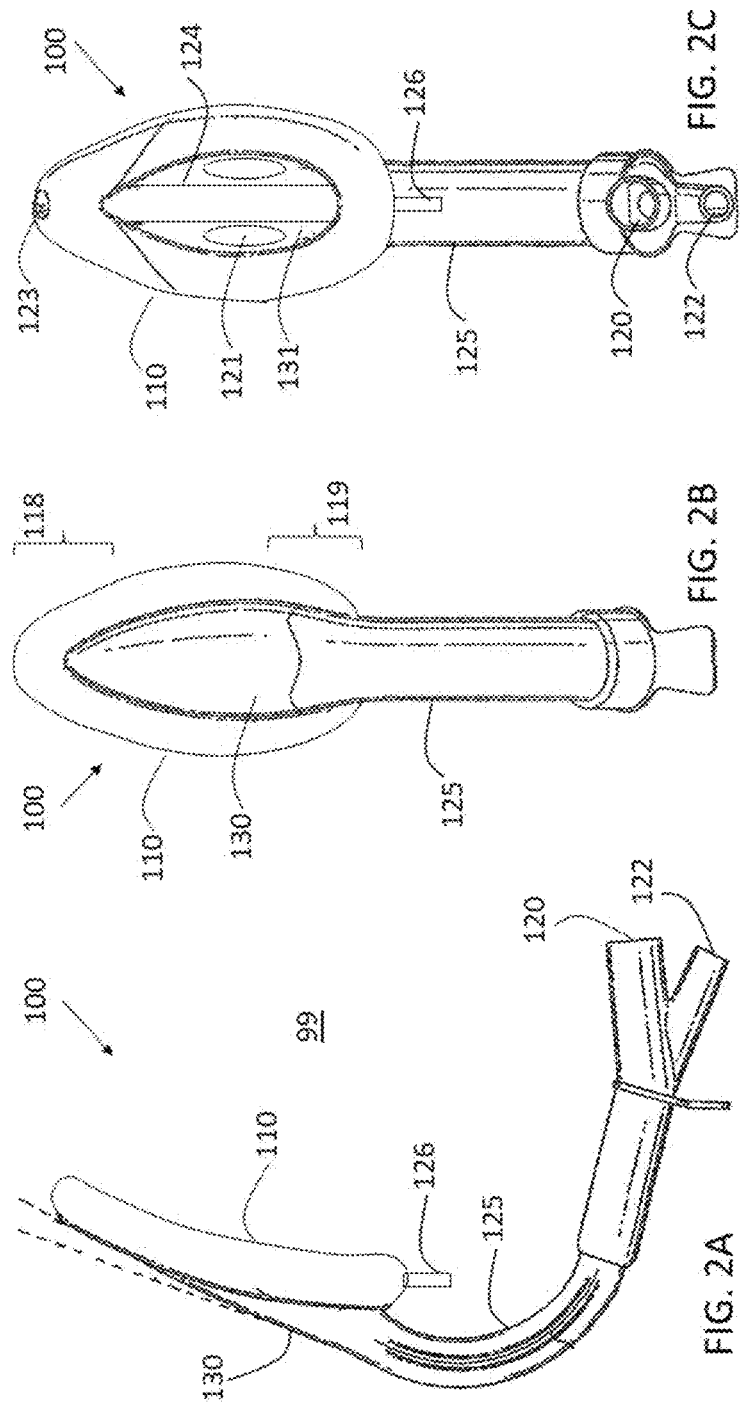

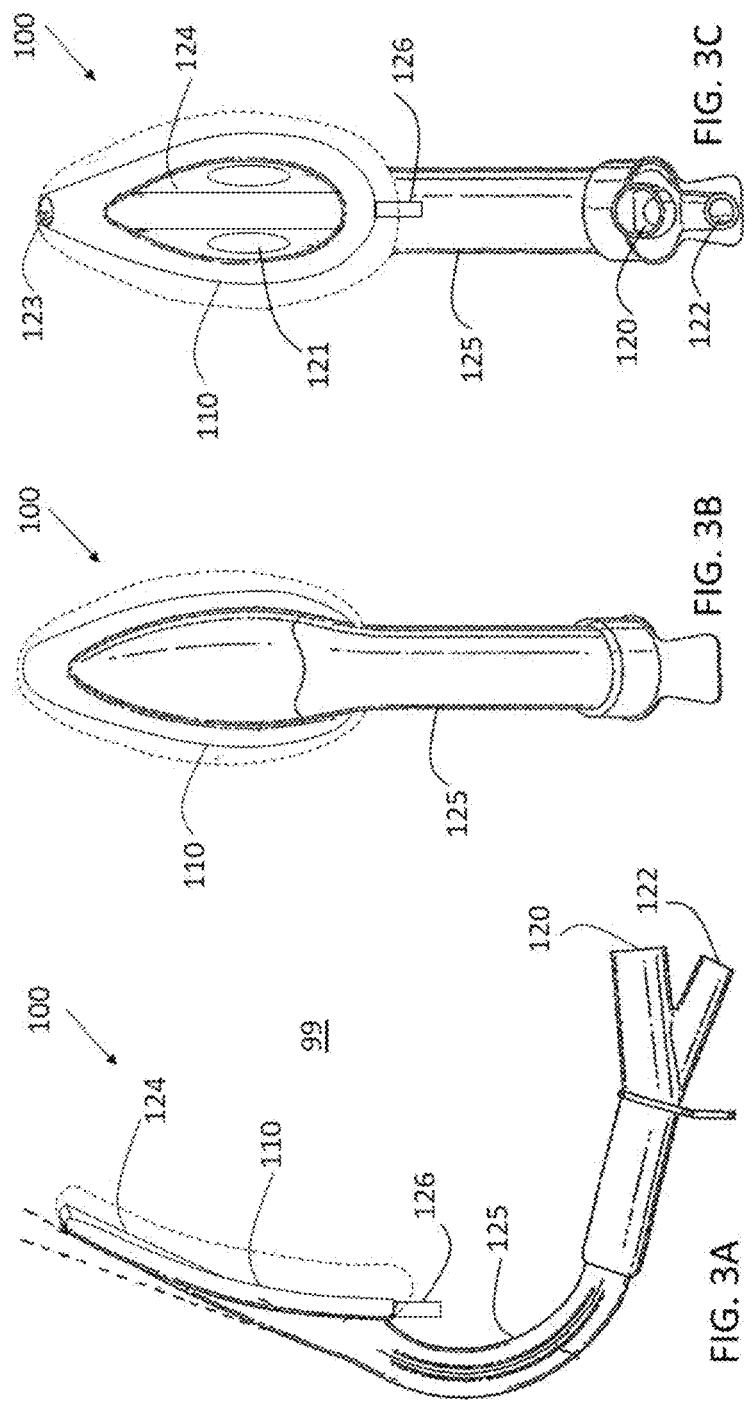

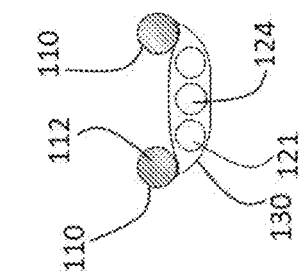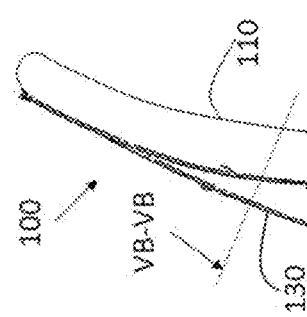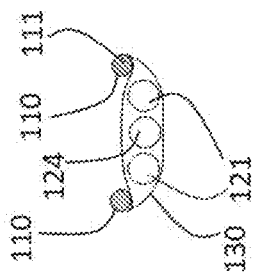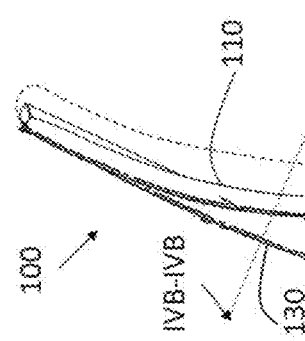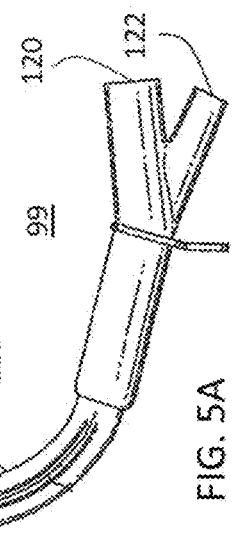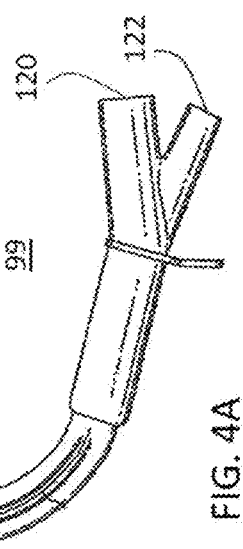

| Fill Volume | KNOWN DEVICE A Pressure [cmH2O] | KNOWN DEVICE B Pressure [cmH2O] | Invention Embodiment Pressure [cmH2O] |
|---|---|---|---|
| 0 | -100 | -100 | -100 |
| V1 | 10 | 10 | 10 |
| V1 + 10% | 39.7 | 40.1 | 14.5 |
| V1 + 20% | 80.0 | 72.1 | 18.7 |
| V1 + 30% | >140 | 103.0 | 22.5 |
| V1 + 40% |  | 135.0 | 25.5 |

FIG. 8

LARYNGEAL MASK CUFF

CROSS-REFERENCE TO RELATED APPLICATIONS

The present application claims the benefit of U.S. Provisional Application 62/592,020, filed Nov. 29, 2017, which is assigned to the assignee of the present application and is incorporated herein by reference.

FIELD OF THE APPLICATION

The present invention relates generally to lung ventilation devices, and specifically to laryngeal mask airway devices (LMA devices).

BACKGROUND OF THE APPLICATION

Laryngeal mask airway devices (LMA devices) are useful in facilitating lung ventilation by forming a low-pressure seal around the patient's laryngeal inlet, thereby avoiding the known harmful effects of endotracheal tube (ETT) devices, which form a seal within the trachea. LMA devices have become standard medical devices, instead of ETT devices, for rapidly and reliably establishing an unobstructed airway in a patient in emergency situations and in the administration of anesthetic gases. Some LMA devices further include a drainage tube, which opens into the distal tip of the mask and emerges from the mouth of the patient.

During general anesthesia, pulmonary ventilation is secured with an ETT device or by a LMA device, and attention to the risk of complications related to a high intracuff pressure is important. When the cuff-to-tracheal wall pressure exceeds the tracheal capillary pressure (130-140 cm H2O) for approximately 15 minutes, the tracheal mucous membrane becomes ischemic. The intracuff pressure approximates the cuff-to-tracheal wall pressures in high volume/low pressure cuffs, and a cuff pressure below 120 cm H2O is recommended to prevent ischemic injury. In addition, recurrent laryngeal nerve palsy has been demonstrated in up to 5% of patients after intubation, and a high cuff pressure is suspected as contributing to this complication. Similarly, in patients provided with a laryngeal mask, a high cuff pressure may lead to palsy of the lingual, hypoglossal, and recurrent laryngeal nerves, and postoperative sore throat.

The risk during anesthesia with nitrous oxide (NO) is further complicated by the fact that NO gases penetrate the cuff, thereby gradually increasing the cuff pressure above the initial setting at which the cuff was inflated.

U.S. Pat. Nos. 8,783,256, 5,632,271, and 7,305,985, all to Brain, describe laryngeal mask airway devices.

Rokamp K Z et al., in "Tracheal tube and laryngeal mask cuff pressure during anaesthesia—mandatory monitoring is in need," BMC Anesthesiology December 2010 10:20, describe "a prospective quality-control study," in which "201 patients undergoing surgery during anaesthesia (without the use of nitrous oxide) were included for determination of the cuff pressure of the tracheal tubes and laryngeal masks" (abstract).

A "Quick Reference Guide," Teleflex (Triangle Park, N.C., USA), 2013, lists various LMA Airways, having different sizes and maximum cuff volumes.

SUMMARY OF THE APPLICATION

Embodiments of the present invention provide a laryngeal mask airway (LMA) device, which comprises an inflatable annular cuff that is insertable through a mouth of a patient to an inserted location within the patient, such that an anterior side of the cuff forms a seal around a laryngeal inlet of the patient upon inflation of the cuff. When the cuff is inflated to a working medium pressure, the LMA device is suitable for facilitating lung ventilation. For example, the working medium pressure may be between 15 and 120 cm H2O, such as between 15 and 100 cm H2O, e.g., between 15 and 50 cm H2O, such as between 15 and 40 cm H2O.

The cuff, when disposed in free space, is characterized by a pressure-volume curve that represents the pressure in the cuff when inflated to different volumes of the cuff that include a low-pressure volume corresponding to a low pressure of 10 cm H2O. The pressure-volume curve includes a local maximum pressure at a medium volume of the cuff between 1.25 and 2.4 times the low-pressure volume, such as between 1.5 and 2.2 times the low-pressure volume, e.g., between 1.8 and 2.2 times the low-pressure volume. Typically, the local maximum pressure is between 15 and 120 cm H2O, such as between 15 and 100 cm H2O, e.g., between 15 and 60 cm H2O, such as between 15 and 40 cm H2O, e.g., between 15 and 30 cm H2O (the maximum clinically-allowed pressure in LMA devices is 60 cm H2O).

The pressure-volume curve also includes respective high-volume medium pressures corresponding to all high volumes of the cuff that are between 2.5 and 3 times the low-pressure volume. Each of the high-volume medium pressures is (a) less than the local maximum pressure, and (b) typically between 15 and 120 cm H2O, e.g., between 15 and 50 cm H2O, such as between 15 and 40 cm H2O. Therefore, even if the cuff is inflated to a volume substantially greater than the recommended volume, the pressure in the cuff cannot increase to levels that might cause soft tissue ischemia.

In order to provide the pressure-volume curve described above, the cuff comprises a highly elastic material that results in substantial expansion of the cuff upon incremental inflation. For example, the cuff may comprise non-latex synthetic polyisoprene, e.g., primarily non-latex synthetic polyisoprene by weight.

By contrast, conventional LMA devices employ cuffs having little elasticity at the working inflation pressure range of less than 60 cm H2O. Conventional LMA devices generally have a wall thickness that is at least 0.2 mm, and a durometer hardness such that there is little difference (less than 10%) in the volume of conventional cuffs between a pressure of 10 cm H2O and any other pressure between 15 cm H2O and 40 cm H2O. As a result, small increases in inflation volume of conventional cuffs result in large increases in pressure.

As a result of the above-mentioned properties, the LMA device of the present invention has good tissue-conforming properties and low sensitivity to cuff inflation volume variations. The cuff of the present invention creates a good seal even at lower cuff pressures. The cuff pressure is less sensitive to restriction by boundary tissue contours than are conventional LMA cuffs. In addition, at working pressures, increases in inflation volume result predominantly in inflation of cuff regions with lower sealing pressure, thereby improving the seal in the most needed locations around the cuff perimeter.

By contrast, conventional LMA cuffs generally can establish a good seal with surrounding tissue only at high cuff pressure; as a result, recommended cuff pressures generally are above 50 cm H2O. This high pressure substantially limits the duration of ventilation with conventional LMA devices, in order to avoid a high risk of soft tissue ischemic.

Moreover, in conventional LMA cuffs even small increases in inflation with ambient-pressure air result in large increases in pressure in the cuffs. Experiments conducted by the inventor demonstrated that the recommended "upper volume limits" of inflation of conventional LMA cuffs result in a cuff pressure greater than 100 cm H2O, which would put patients at risk of soft tissue ischemia within as little as 30 minutes.

In addition, since conventional LMA cuffs comprise low-compliance materials, adult-size LMA devices have a large pre-inflation cuff tube diameter in the range of 12 to 16 mm. Because conventional cuffs have little compliance, their cross-sectional area and volume increases by less than 25% when inflated to any working pressure between 20 and 60 cm H2O compared with the cross-sectional area and volume at a low pressure of 10 cm H2O. Conventional cuffs do not conform to the oral cavity tissue contours, but instead are pushed by the oral cavity to increase the cuff pressure further and simultaneously generate high pressure on particular tissue contours while having low sealing pressures on other portions of the oral cavity tissue.

There is therefore provided, in accordance with an application of the present invention, apparatus including a laryngeal mask airway (LMA) device including:

an inflatable annular cuff, which is insertable through a mouth of a patient to an inserted location within the patient, such that an anterior side of the cuff forms a seal around a laryngeal inlet of the patient upon inflation of the cuff;

a backplate attached to the cuff; and an airway tube having (a) a proximal end that is configured to be disposed outside the patient's mouth when the cuff is at the inserted location, and (b) a distal end that is in fluid communication with a port of the backplate, wherein the port is open through a hollow center of the annular cuff, wherein the cuff, when disposed in free space, is characterized by a pressure-volume curve that represents the pressure in the cuff when inflated to different volumes of the cuff that include a low-pressure volume corresponding to a low pressure of 10 cm H2O, wherein the pressure-volume curve includes:

a local maximum pressure at a medium volume of the cuff
  between 1.25 and 2.4 times the low-pressure volume, wherein the local maximum pressure is between 15 and 120 cm H2O, and
respective high-volume medium pressures corresponding to
  all high volumes of the cuff that are between 2.5 and 3 times the low-pressure volume, wherein each of the high-volume medium pressures is between 15 cm H2O and 99% of the local maximum pressure.

For some applications, each of the high-volume medium pressures is less than 95% of the local maximum pressure, such as less than 90% of the local maximum pressure.

For some applications, the local maximum pressure is less than 60 cm H2O, such as less than 40 cm H2O, e.g., less than 30 cm H2O.

For some applications, the local maximum pressure is greater than 20 cm H2O.

For some applications, the pressure-volume curve has the local maximum pressure at a medium volume that is between 1.5 and 2.2 times the low-pressure volume.

For some applications, the pressure-volume curve has the local maximum pressure at a medium volume that is between 1.8 and 2.2 times the low-pressure volume.

For some applications, the cuff is configured such that when disposed in free space and inflated to the low-pressure volume of the cuff, further inflation of the cuff with an incremental quantity of air results in a medium pressure in the cuff that is less than 30 cm. H2O, the incremental quantity of air having a volume, when the air is at ambient pressure, equal to 10% of the low-pressure volume of the cuff.

For some applications, the cuff is configured such that when disposed in free space and inflated to the low-pressure volume of the cuff, further inflation of the cuff with an incremental quantity of air results in a medium pressure in the cuff that is less than 60 cm H2O, the incremental quantity of air having a volume, when the air is at ambient pressure, equal to 20% f the low-pressure volume of the cuff.

For some applications:
  the cuff is configured such that when disposed in free space and inflated to one of the high volumes of the cuff corresponding to a first pressure in the cuff, further inflation of the cuff with an incremental quantity of air results in a second pressure in the cuff that is less than the first pressure, and
  the incremental quantity of air has a volume, when the air is at ambient pressure, equal to 10% of the one of the high volumes of the cuff.

For some applications:
  the cuff is configured such that when disposed in free space and inflated to one of the high volumes of the cuff corresponding to a first pressure in the cuff, further inflation of the cuff with an incremental quantity of air results in a second pressure in the cuff that is less than the first pressure, and
  the incremental quantity of air has a volume, when the air is at ambient pressure, equal to 30% of the one of the high volumes of the cuff.

For some applications, the backplate is attached to the cuff only at locations on a posterior side of the cuff.

For some applications, the apparatus further includes a drainage tube extending from a location near a distal end of the cuff to a location outside the patient's mouth when the cuff is at the inserted location.

For any of the applications described above, the cuff may include non-latex synthetic polyisoprene. For some applications, the cuff includes primarily non-latex synthetic polyisoprene by weight.

For any of the applications described above, the thickness of a wall of the cuff may be between 0.05 mm and 0.5 mm at the thinnest of non-attached locations of the cuff that are not attached to the backplate, such as between 0.05 mm and 0.3 mm at the thinnest of the non-attached locations, e.g., between 0.06 mm and 0.1 mm at the thinnest of the non-attached locations.

For any of the applications described above, the cuff, when disposed in free space and inflated to the low-pressure volume of the cuff, may have an asymmetric toroidal tubular shape. For some applications, the cuff, when disposed in free space and inflated to the low-pressure volume of the cuff, has an average low-pressure external cross-sectional area, measured perpendicular to the center line of the cuff, that is less than 225 mm2, such as less than 144 mm2, e.g., less than 81 mm2.

There is further provided, in accordance with an application of the present invention, a method including:

inserting an inflatable annular cuff of a laryngeal mask airway (LMA) device through a mouth of a patient to an inserted location within the patient, such that a proximal end of an airway tube of the LMA device is disposed outside the patient's mouth, and a distal end of the airway tube is in fluid communication with a port of a backplate of the LMA device attached to the annular cuff, wherein the port is open through a hollow center of the annular cuff; and inflating the cuff such that an anterior side of the cuff forms a seal around a laryngeal inlet of the patient, wherein the cuff, when disposed in free space, is characterized by a pressure-volume curve that represents the pressure in the cuff when inflated to different volumes of the cuff that include a low-pressure volume corresponding to a low pressure of 10 cm H2O, wherein the pressure-volume curve includes:

a local maximum pressure at a medium volume of the cuff between 1.25 and 2.4 times the low-pressure volume, wherein the local maximum pressure is between 15 and 120 cm H2O, and respective high-volume medium pressures corresponding to all high volumes of the cuff that are between 2.5 and 3 times the low-pressure volume, wherein each of the high-volume medium pressures is between 15 cm H2O and 99% of the local maximum pressure.

For some applications, inserting the annular cuff includes inserting the annular cuff such that a drainage tube of the LMA device extends from a location near a distal end of the cuff to a location outside the patient's mouth when the cuff is at the inserted location.

The present invention will be more fully understood from the following detailed description of embodiments thereof, taken together with the drawings, in which:

BRIEF DESCRIPTION OF THE DRAWINGS

FIGS. 2A-C are schematic illustrations of respective views of the LMA device of FIG. 1 with a cuff thereof inflated to a working medium volume, in accordance with an application of the present invention;

FIGS. 3A-C are schematic illustrations of respective views of the LMA device of FIG. 1 with a cuff thereof inflated to a low-pressure volume, in accordance with an application of the present invention;

FIGS. 4A-B are schematic illustrations of the LMA device of FIG. 1 with a cuff thereof inflated at a low pressure, in accordance with an application of the present invention;

FIGS. 5A-B are schematic illustrations of the LMA device of FIG. 1 with a cuff thereof inflated at a working medium pressure, in accordance with an application of the present invention;

FIG. 8 is a table that shows the results of an experiment conducted on behalf of the inventor, in accordance with an application of the present invention;

DETAILED DESCRIPTION OF APPLICATIONS

Figure 1:
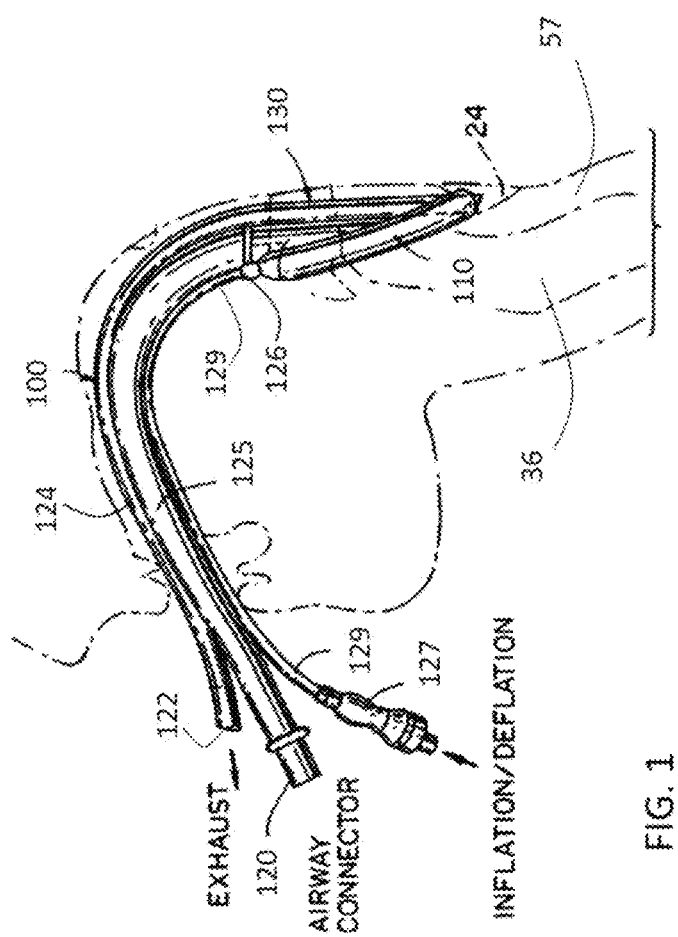
FIG. 1 is a schematic illustration of a laryngeal mask airway (LMA) device, in accordance with an application of the present invention.

FIG. 1 is a schematic illustration of a laryngeal mask airway (LMA) device 100, in accordance with an application of the present invention. In typical use, LMA device 100 is inserted into the throat while deflated (the upper surface of the throat is bounded by hard and soft palates). LMA device 100 is lodged in the pharynx at the base of the hypopharynx 24 where the throat divides into the trachea 36 and the esophagus 57. Typically, after LMA device 100 is thus lodged in the pharynx, an inflatable annular cuff 110 of LMA device 100 is inflated at the inserted location with the patient, as illustrated in FIG. 1.

Reference is still made to FIG. 1 and is additionally made to FIGS. 2A-C, which are schematic illustrations of respective views of LMA device 100 with cuff 110 inflated to a working medium volume, as described hereinbelow with reference to FIGS. 5A-B, in accordance with an application of the present invention.

Reference is yet additionally made to FIGS. 3A-C, which are schematic illustrations of respective views of LMA device 100 with cuff 110 inflated to a low-pressure volume, as described hereinbelow with reference to FIGS. 4A-B, in accordance with an application of the present invention. FIGS. 3A-C also show in phantom cuff 110 inflated to the working medium volume shown in FIGS. 2A-C.

LMA device comprises an airway tube 125, which is installed through the mouth of the patient. Airway tube 125 has a proximal end 120 that is configured to be disposed outside the patient's mouth when the cuff is at the inserted location. Proximal end 120 typically defines an airway connector port, which is configured for connection to air or other ventilating apparatus for the patient's lungs.

LMA device 100 further comprises a backplate 130 having an airway port 121 (shown in FIG. 2C) through which airway tube 125 can establish a free externally accessible ventilation passage, via the patient's mouth and throat, and past the epiglottis to the larynx. Airway tube 125 has a distal end that is in fluid communication with airway port 121. Airway port 121 is open through a hollow center of annular cuff 110. For example, backplate 130 may comprise an elastomer such as silicone rubber, PVC, or polyurethane, which may be the same material as or a different material from the cuff balloon, and may be relatively stiff due to its thickness of more than 1 mm. Backplate 130 typically has a one-piece, integral spoon-shape having an oval portion. Opposite sides of the oval portion are typically defined by a convex pharyngeal side and a concave laryngeal side. The periphery of the oval portion is hermetically bonded to the periphery of cuff 110, so as to establish, when placed within the human patient, separation between a laryngeal chamber region 131 and a pharyngeal region on the other side of backplate 130.

Inflatable annular cuff 110 is insertable through a mouth of a patient to an inserted location within the patient, typically when the cuff is deflated, such that an anterior side of the cuff forms a seal around a laryngeal inlet of the patient upon inflation of the cuff. Backplate 130 is attached to, and typically surrounded by, cuff 110. Optionally, backplate 130 is attached to cuff 110 at locations that are closer to a posterior side of the cuff than to an anterior side of the cuff. Optionally, backplate 130 is attached to cuff 110 only at locations on the posterior side of cuff 110. For some applications, LMA device 100 further comprises a drainage tube 124 extending from a distal drainage port 123 at a location near a distal end of cuff 110 to a proximal drainage port 122 at a location outside the patient's mouth when cuff is at the inserted location.

LMA device 100 further comprises an externally-accessible inflation tube 129 and an inflation port 126 on cuff 110 for supplying air to the cuff and extracting air from (and therefore collapsing) the cuff, for inserting the cuff into and removing the cuff from the patient. Typically, an inflation check valve 127 is disposed in inflation tube 129 for holding a given inflation of cuff 110. Typically, though not necessarily, before cuff 110 is inserted to the patient, an inflation/deflation device is actuated to apply a vacuum, via inflation tube 129, to the interior of cuff 110 sufficient to fully deflate the cuff prior to insertion of the cuff through the mouth of the patient. For concreteness of discussion and test procedures, initial inflation volumes are assumed to start from a deflated state in which the cuff is deflated at suction pressure of negative 100 cm H2O (−100 cm H2O).

In the installed position shown in FIG. 1, a projecting but blunted distal region 118 (labeled in FIG. 2B) of cuff 110 is shaped to conform with the base of hypopharynx 24.

In some applications of the present invention, such as shown in FIGS. 2A-C, LMA device 100 is of the gastro-laryngeal mask (GLM) type, in which drainage tube 124 having a proximal drainage port 122 and a distal drainage port 123 (labeled in FIG. 2C), which enables extraction and external removal of gastric-discharge products from esophagus 57. Drainage tube 124 follows the general course of airway tube 125, provides sealed passage through the interior of cuff 110, and is open through distal region 118 of the cuff. Such GLM devices are commonly used in hospital settings in which evacuation suction sources are available, while simpler configurations of LMA devices without evacuation tubes are more commonly used in emergency intubations settings. Although the figures show drainage tube 124, drainage tube 124 is not an essential element of LMA device 100, and is not provided in some embodiments of the invention. Therefore, unless specifically stated to the contrary, all features of LMA device 100 described herein apply to LMA designs both with and without drainage tube 124.

Reference is now made to FIGS. 4A-B and 5A-B, which are schematic illustrations of LMA device 100 with cuff 110 inflated at a low pressure and a working medium pressure, respectively, in accordance with an application of the present invention. FIGS. 4B and 5B are cross-sectional views take along lines IVB-IVB of FIG. 4A and VB-VB of FIG. 5A, respectively. FIG. 4A also shows in phantom cuff 110 inflated to the working medium volume shown in FIG. 5A.

When cuff 110 is inflated to the low pressure illustrated in FIGS. 4A-B, LMA device 100 is unsuitable for facilitating lung ventilation. For example, the low pressure may be 10 cm. H2O. At this low pressure, cuff 110 has a first cross section 111, measured perpendicular to the center line of the cuff; the first cross section 111 has a first area. For some applications, cuff 110, when disposed in free space and inflated to the low-pressure volume of the cuff, has an average low-pressure external cross-sectional area, measured perpendicular to the center line of the cuff, that is less than 225 mm2, such as less than 144 mm2, e.g., less than 81 mm2.

As used in the present application, including in the claims, "disposed in free space" means disposed in ambient air 99 at atmospheric pressure at 20 degrees Celsius without being constrained by the patient's anatomy, a delivery tool, or anything else. As used in the present application, including in the claims, the "center line" of the cuff is the set of all centroids of transverse cross-sectional sections of the cuff along the cuff. Thus the cross-sectional sections are locally perpendicular to the center line, which runs along the cuff. (If the cuff is circular in cross-section, the centroids correspond with the centers of the circular cross-sectional sections.) In the present application, including in the claims, all pressures are gauge pressures that are zero-referenced against ambient air 99 pressure.

When cuff 110 is inflated to the working medium pressure illustrated in FIGS. 5A-B, LMA device 100 is suitable for facilitating lung ventilation. For example, the working medium pressure may be between 15 and 120 cm H2O, such as between 15 and 100 cm H2O, e.g., between 15 and 50 cm H2O, such as between 15 and 40 cm H2O. At the working medium pressure, cuff 110 has a second. cross section 112, measured perpendicular to the center line of the cuff; the second cross section 112 has a second area greater than the first area. Typically, cuff 110, when disposed in free space and inflated to the working medium. volume of the cuff, has an asymmetric toroidal tubular shape, generated, for example, by an asymmetrical oval or ellipse having a wider proximal 20% region 119 and narrower distal 20% region 118.

Figure 6:
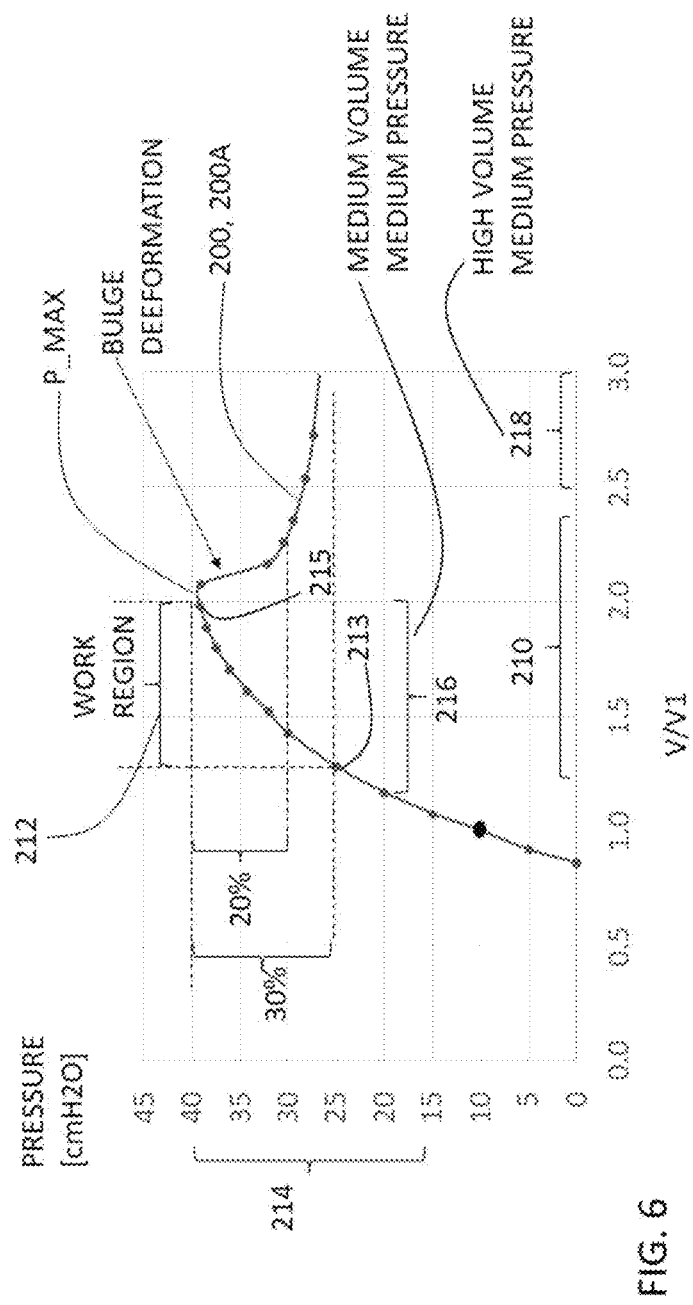
FIG. 6 includes an exemplary pressure-volume curve, in accordance with an application of the present invention.

Reference is now made to FIG. 6, which includes a pressure-volume curve 200, in accordance with an application of the present invention. Cuff 110, when disposed in free space, is characterized by pressure-volume curve 200, which represents the pressure in cuff 110 when inflated to different volumes of cuff 110 that include a low-pressure volume V1 corresponding to a low pressure of 10 cm H2O. Pressure-volume curve 200 illustrated in FIG. 6 is an exemplary pressure-volume curve 200R; a large number of additional pressure-volume curves having the general properties of pressure-volume curve 200 are possible, and are within the scope of the present invention. For example, another exemplary pressure-volume curve 200B is described hereinbelow with reference to FIG. 7.

Pressure-volume curve 200 includes a local maximum. pressure $P_{MAX}$ of cuff 110 at a medium volume within a medium-volume range 210 between 1.25 and 2.4 times the low-pressure volume V1, such as between 1.5 and 2.2 times the low-pressure volume V1, e.g., between 1.8 and 2.2 times the low-pressure volume V1. Typically, the local maximum pressure $P_{MAX}$ is between 15 and 120 cm H2O, such as between 15 and 100 cm H2O, e.g., between 15 and 60 cm H2O, such as between 15 and 40 cm H2O, e.g., between 15 and 30 cm H2O (the maximum clinically-allowed pressure in LMA devices is 60 cm H2O). For some applications, the low end of these ranges is 20 cm H2O.

"Medium pressure" is defined as a medium-pressure range 214 between 15 cm H2O and the local maximum pressure $P_{MAX}$. A medium-pressure volume range 216 is defined as the range of volumes between a low-end volume corresponding to the pressure of 15 cm H2O and a high-end volume at the local maximum pressure $P_{MAX}$. Hence medium-pressure volume range 216 is the range of medium-volume medium-pressures.

A working medium-pressure volume range 212 has a low-end volume 213 and high-end. volume 215, the low-end volume 213 less than the high-end volume 215. For example, low-end volume 213 may be:
between 20 and 25 cm H2O, or
between 20% and 30% less than the local maximum pressure $P_{MAX}$.

For example, high-end volume 215 may be:
between 40 and 60 cm H2O, or
equal to the local maximum pressure $P_{MAX}$, i.e., before the creation of bulge deformation 320 described hereinbelow with reference to FIGS. 9A-D.

By way of example, in FIG. 6 low-end volume 213 is labeled at 25 cm H2O and high-end volume 215 is labeled at the local maximum pressure $P_{MAX}$.

Figure 7:
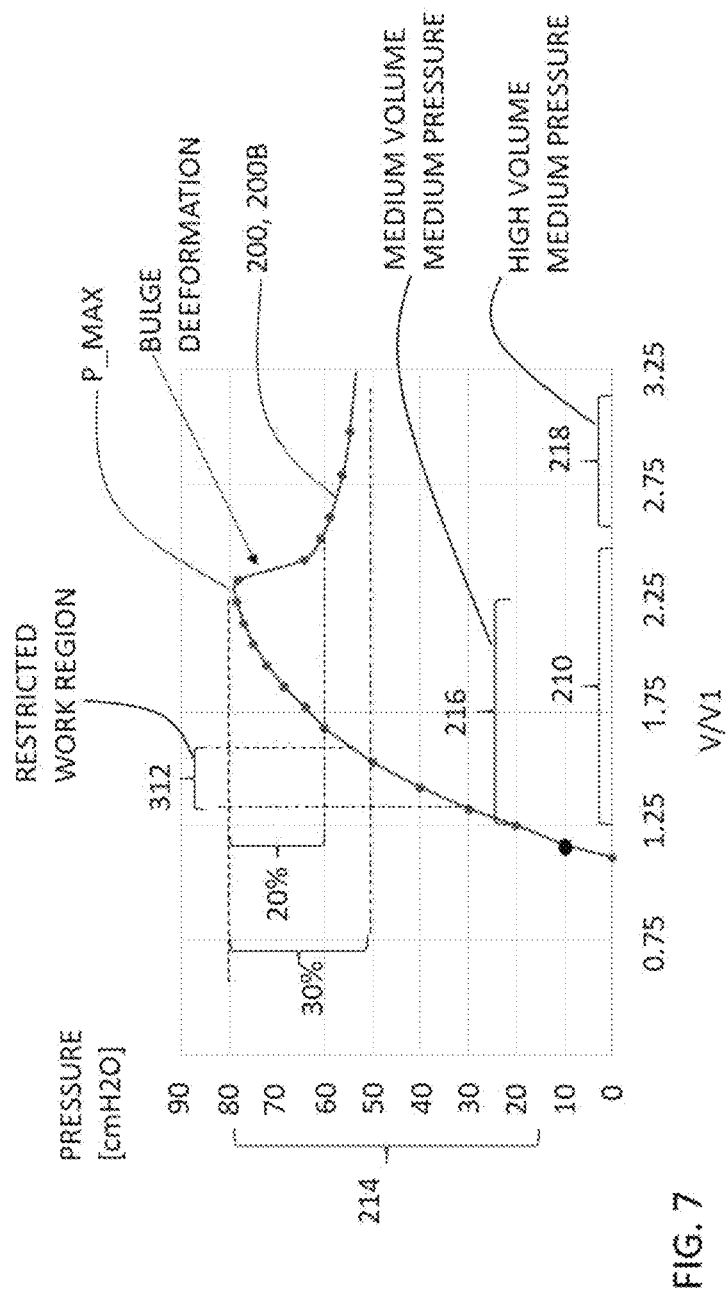
FIG. 7 includes another exemplary pressure-volume curve, in accordance with an application of the present invention.

Working medium-pressure volume range 212 may vary in different configurations, as exemplified in the two graphs of FIGS. 6 and 7. In order to achieve both pressure safety and a good seal, in some configurations the local maximum pressure $P_{MAX}$ greater than 25 cm H2O but not more than. 40 cm H2O, as exemplified in the graph of FIG. 6.

Pressure-volume curve 200 also includes respective high volume medium pressures (labeled as a high-volume medium-pressure range 218) corresponding to all high volumes of cuff 110 that are between 2.5 and 3 times the low-pressure volume V1. Each of the high-volume medium pressures is typically between 15 and 99% of the local maximum pressure $P_{MAX}$, such as less than 95%, e.g., less than 90%, of the local maximum pressure $P_{MAX}$, and/or less than 60 cm H2O, such as less than 40 cm H2O), e.g., less than 30 cm H2O). Therefore, even if cuff 110 is inflated to a volume substantially greater than the recommended volume, the pressure in the cuff cannot increase to levels that might cause soft tissue ischemia.

In order to provide pressure-volume curve 200 described above, cuff 110 comprises a highly elastic material that results in substantial expansion of the cuff upon incremental inflation. For example, cuff 110 may comprise non-latex synthetic polyisoprene, e.g., primarily non-latex synthetic polyisoprene by weight; for some applications, the thickness of a wall of cuff 110 is between 0.05 mm and 0.5 mm, e.g., between 0.05 and 0.3 mm, such as between 0.05 and 0.2 mm, such as between 0.06 mm and 0.1 mm, at the thinnest of non-attached locations of cuff 110 that are not attached to backplate 130. Alternatively, for example, cuff 110 may comprise silicone, e.g., primarily silicone by weight; for some applications, the thickness of a wall of cuff 110 is between 0.05 mm and 0.5 mm, e.g., between 0.05 and 0.3 mm, such as between 0.05 and 0.2 mm, such as between 0.06 mm and 0.1 mm, at the thinnest of non-attached locations of cuff 110 that are not attached to backplate 130; alternatively or additionally, for some applications, the silicone has a hardness of less than Shore A50, less than Shore A30, or less than Shore OO-60.

By contrast, conventional LMA devices employ cuffs having little elasticity at the working inflation pressure range of less than 60 cm H2O, such that there is an increase of less than 20% in the volume of conventional cuffs between a pressure of 10 cm H2O and any other pressure between 15 and 40 cm H2O (see, for example, the test table described with reference to FIG. 8 hereinbelow).

For some applications, cuff 110 is configured such that when disposed in free space and inflated to one of the high volumes of cuff 110 corresponding to a first pressure in cuff 110 between 2.5 and 3 times the low-pressure volume V1, further inflation of cuff 110 with an incremental quantity of air results in a second pressure in cuff 110 that is less than the first pressure. The incremental quantity of air has a volume, when the air is at ambient pressure, equal to 10% of the one of the high volumes of cuff 110.

For some applications, cuff 110 is configured such that when disposed in free space and inflated to one of the high volumes of cuff 110 corresponding to a first pressure in cuff 110 between 2.5 and 3 times the low-pressure volume V1, further inflation of cuff 110 with an incremental quantity of air results in a second pressure in cuff 110 that is less than the first pressure. The incremental quantity of air has a volume, when the air is at ambient pressure, equal to 30% of the one of the high volumes of cuff 110.

Reference is still made to FIG. 6. During use of DMA device 100 after cuff 110 has been placed at the inserted location, as shown in FIG. 1, cuff 110 is ideally inflated to:

a volume equal to between 60% (e.g., 70%) and 100% (e.g., 90%) of the volume of cuff 110 that corresponds to the local maximum pressure $P_{MAX}$, described hereinabove with reference to FIG. 6, a pressure equal to between 70% (e.g., 80%) and 100% (e.g., 95%) of the local maximum pressure $P_{MAX}$, described hereinabove with reference to FIG. 6, and/or a pressure greater than 20 cm H2O (e.g., greater than 25 cm H2O, such as greater than 30 cm H2O) and less than the local maximum pressure $P_{MAX}$.

Moreover, cuff 110 typically works well when inflated to all volumes in the above-mentioned working medium-pressure volume range 212.

In practice, the healthcare worker typically inflates cuff 110 with a known quantity of ambient-pressure air, rather than to a certain pressure, because the pressure is typically not measured during or after inflation of cuff 110.

LMA device 100 is typically accompanied by instructions for use that specify a narrow range of quantities of ambient-pressure air, e.g., 25 to 30 cc for a standard adult-size cuff. The range of air quantities is ascertained by the manufacturer for each configuration of LMA device 100, based in large part on pressure-volume curve 200 of cuff 110. Ideally, the specified range of quantities of air results in working medium-pressure volume range 212 described above. However, because of the shape of pressure-volume curve 200 of cuff 110, moderate underinflation and even substantial over-inflation still results in a working medium pressure that is suitable for facilitating lung ventilation, without any need to measure the pressure in the cuff. In particular, the peak characteristics of pressure-volume curve 200, in configurations in which the peak pressure is less than 60 cm H2O, ensure that even substantial over-inflation (e.g., 20% above maximum recommended inflation) still results in a pressure of less than 60 cm H2O.

Moreover, as illustrated in FIG. 7, described hereinbelow, the relatively gentle slope of pressure-volume curve 200B allows for some clinically applicable (though less optimal) configurations in which the local maximum pressure $P_{MAX}$ has a value up to 120 cm H2O, such as 80 cm H2O, and yet one can define a restricted-working volume range corresponding to pressures less than 60 cm H2O, such as between 30 and 55 cm. H2O, that correspond to a still wide range of inflation volumes of more than 10% greater than V1.

For example, the range of the recommended quantity of ambient-pressure air may be ascertained by the manufacturer by multiplying the medium volume of cuff 110 that corresponds to the local maximum pressure $P_{MAX}$ of cuff 110 by (a) a low-end-range percentage and (b) a high-end-range percentage, resulting in (a) the low end and (b) the high end of the range of the recommended quantity of ambient-pressure air, respectively. For example, the low-end-range percentage may be between 80% and 95%, such as 90%, and the high-end-range percentage may be between 105% and 120%, e.g., 110%.

As mentioned above, pressure-volume curve 200 characterizes cuff 110 when disposed in free space. Nevertheless, when the cuff is placed at the inserted location, the constraints of the anatomy on the cuff typically have only minimal impact on the pressure-volume curve of the cuff, and do not materially increase the pressure in the cuff. By contrast, in convention LMA devices, such constraints generally lead to a significant increase (e.g., by more than 25%, or more than 50%) of the cuff pressure compared to pressure achieved at the same inflation volume when the cuff is disposed in free space.

Reference is now made to FIG. 7, which includes another pressure-volume curve 200, in accordance with an application of the present invention. Pressure-volume curve 200 illustrated in FIG. 7 is an exemplary pressure-volume curve 200B. Pressure-volume curve 200B, like pressure-volume curve 200A described hereinabove with reference to FIG. 6, represents the pressure in cuff 110 when inflated to different volumes of cuff 110 that include a low-pressure volume V1 corresponding to a low pressure of 10 cm H2O.

Pressure-volume curve 200B is similar to pressure-volume curve 200A, except that in pressure-volume curve 200B the local maximum pressure $P_{MAX}$ occurs at a pressure of 80 cm H2O at a medium-pressure volume equal to about 2.25 * V1, while in pressure-volume curve 200A the local maximum pressure $P_{MAX}$ occurs at a pressure of 40 cm H2O at a medium-pressure volume equal to about 2 * V1.

Despite the relatively high, and clinically sub-optimal, local maximum pressure $P_{MAX}$ in pressure-volume curve 200B, the relatively gentle slope of pressure-volume curve 200B allows the definition of a restricted-working volume range 312 corresponding to pressures less than 60 cm H2O, such as between 30 and 55 cm H2O (as labeled), that correspond to a still wide range of inflation volumes of more than 10% greater than V1. In order to provide restricted-working volume range 312, LMA device 100 is typically accompanied by instructions for use that specify a narrow range of quantities of ambient-pressure air, e.g., 25 to 30 cc for a standard adult-size cuff; for example, the quantities of ambient-pressure air may equal between 1.3 and 1.5 * V1 (i.e., the low-pressure volume V1 corresponding to a low pressure of 10 cm H2O).

Reference is made to FIG. 8, which is a table that shows the results of an experiment conducted on behalf of the inventor, in accordance with an application of the present invention. The experiment compared an exemplary implementation of cuff 110 having a pressure-volume curve similar to pressure-volume curve 200A, described hereinabove with reference to FIG. 6, with two following known devices:

an Ambu AuraOnce size #4 laryngeal mask device cuff (Ambu A/S, Ballerup, Denmark) ("Known Device A" in the table), and an LMA Supreme™ size #4 laryngeal mask device cuff (Teleflex Inc., Wayne, Pa., USA) ("Known Device B" in the table).

The experiment began with the filling of each of the cuffs with respective first volumes V1 of air, measured when the air was at ambient pressure, until the respective pressures measured in the cuffs were 10 cm H2O. The first volumes V1 were defined as the quantity of ambient-pressure air added to the cuffs when initially substantially empty of air, i.e., containing a negligible quantity of air when emptied at a negative pressure of −100 cm H2O. These first volumes V1 served as baselines for comparison with pressures achieved upon additional inflation of the cuffs. The measurement apparatus used in the experiment had an upper limit of 140 cm H2O.

Subsequently, each of the cuffs was filled with respective additional volumes of ambient-pressure air in increments equal to 10% of the respective first volumes V1 of air. For example, if a first volume V1 of 30 cc of air for one of the cuffs, measured at ambient pressure, results in the pressure of 10 cm H2O, the cuff was subsequently inflated with an additional 3 cc of ambient-pressure air (i.e., 10% of the first volume V1), and the resulting pressure in the cuff was measured. The cuff was then inflated with yet additional 3 cc of ambient-pressure air (i.e., 10% of the first volume V1, for a total incremental volume equal to 20% of the first volume V1), and the resulting pressure in the cuff was again measured.

As can be seen, additional inflation of exemplary cuff 110, in accordance with an embodiment of the present invention, results in substantially lower increases in pressure in exemplary cuff 110 than occurred upon corresponding additional inflation of the known cuffs. In particular, at additional inflation volumes of up to 40% of the first volume V1, the pressure in exemplary cuff 110 did not exceed 30 cm H2O, and thus remained in a safe pressure range. Cuff 110 of the present invention typically only attains less than 70% of its working volume at a low inflation pressure of 10 cm H2O. Further inflation by an additional 10% to 30% of the first volume V1 results in a significant increase of cuff 110 volume and only a relatively small increase (typically, less than 100%) in the cuff 110 pressure, which is unlikely to cause soft tissue ischemia.

By contrast, cuff pressure in the known cuffs continuously increased with increases of inflation volume. At additional inflation volumes of as little as 20% of the respective first volumes V1, the pressures in the known cuffs rose to high levels that might cause soft tissue ischemia during ordinary use. This occurs because knowns cuffs substantially attain their working volumes at low inflation pressures, such as 10 cm H2O. Further inflation by an additional 10% to 30% of the inflation volume corresponding to a pressure 10 cm H2O results in only a small increase of the cuff volume and a large increase (typically greater than 100%) in the cuff pressure.

For some applications, cuff 110 is configured such that when disposed in free space and inflated to the low-pressure volume V1 of cuff 110 (that corresponds to the low pressure of 10 cm H2O), further inflation of cuff 110 with an incremental quantity of air results in a medium pressure in cuff 110 that is less than 30 cm H2O, the incremental quantity of air having a volume, when the air is at ambient pressure, equal to 10% of the low-pressure volume V1 of cuff 110. For some applications, cuff 110 is configured such that when disposed in free space and inflated to the low-pressure volume V1 of cuff 110 (that corresponds to the low pressure of 10 cm H2O), further inflation of cuff 110 with an incremental quantity of air results in a medium pressure in cuff 110 that is less than 60 cm H2O, the incremental quantity of air having a volume, when the air is at ambient pressure, equal to 20% of the low-pressure volume V1 of cuff 110.

As used in the present application, including in the claims, the terms "proximal" and "distal" refer to locations nearer to the operator and to the inside of the body, respectively.

In some applications of the present invention, a laryngeal mask airway (LMA) device 100 is provided that comprises:

an inflatable annular cuff 110, which is insertable through a mouth of a patient to an inserted location within the patient, such that an anterior side of cuff 110 forms a seal around a laryngeal inlet of the patient upon inflation of cuff 110;

a backplate 130 attached to cuff 110; and an airway tube 125 having (a) a proximal end 120 that is configured to be disposed outside the patient's mouth when cuff 110 is at the inserted location, and (b) a distal end that is in fluid communication with airway port 121 of backplate 130; airway port 121 is open through a hollow center of cuff 110.

Cuff 110 is configured such that when disposed in free space and inflated to a medium-pressure volume of cuff 110 corresponding to a first pressure in the cuff, further inflation of cuff 110 with an incremental quantity of air results in a second pressure in cuff 110 that is less than the first pressure. The first pressure has a value selected from the range of values between 15 and 60 cm H2O, such as between 15 and 50 cm H2O. The incremental quantity of air has a volume, when the air is at ambient pressure, equal to 10% of the medium-pressure volume of cuff 110.

Figure 9C:
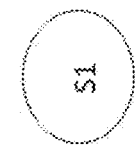
FIGS. 9C and 9D are cross-sectional illustrations of the cuff of FIG. 9B taken along lines IXC-IXC and IXD-IXD, respectively, in accordance with an application of the present invention.
Figure 9D:
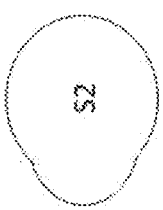
Figure 9B:
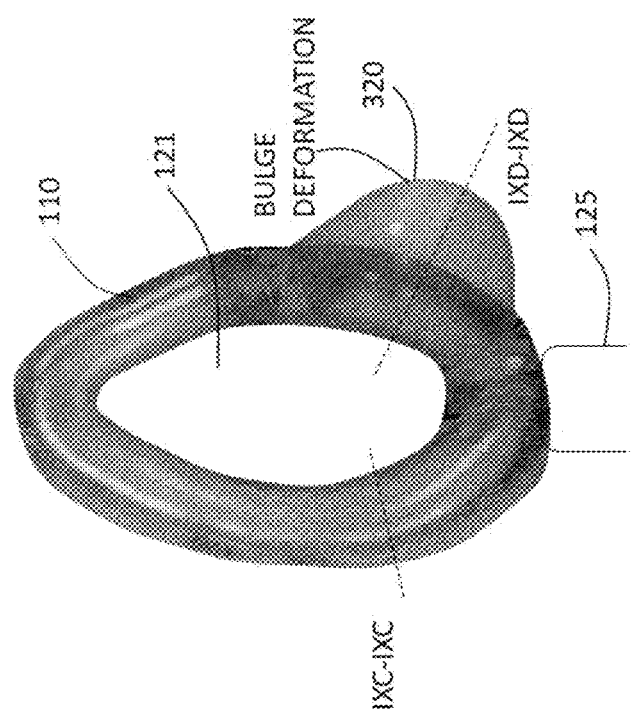
FIGS. 9A and 9B are photographs of an experimental configuration of a cuff of the LMA device of FIG. 1, in accordance with an application of the present invention.

Reference is now made to FIGS. 9. and 9B, which are photographs of an experimental configuration of cuff 110, and FIGS. 9C and 9D, which are cross-sectional illustrations of the cliff of FIG. 9B taken along lines IXC-IXC and IXD-IXD, respectively, in accordance with an application of the present invention. In an experiment performed on behalf of the inventor, an implementation of cuff 110 was constructed and filled to different pressures. The experimental cuff had a pressure-volume curve similar to pressure-volume curve 200, described hereinabove with reference to FIG. 6.

Figure 9A:
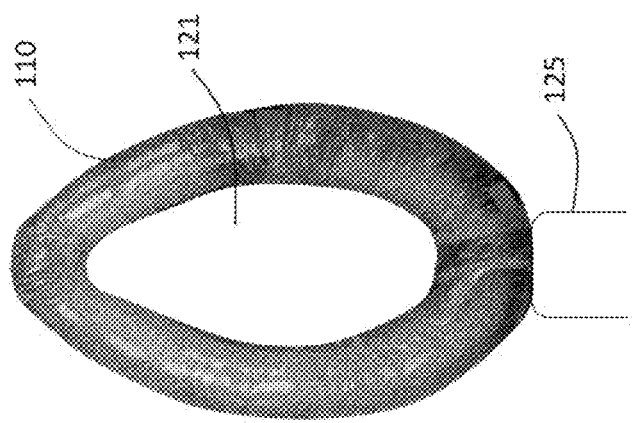

The cuff was first inflated with a first quantity of ambient-pressure air that resulted in a first pressure less than the local maximum pressure $P_{MAX}$ (the first quantity of ambient-pressure air was 1.23 * V1 and the first pressure was 20 cm H2O), resulting in the cuff shape shown in FIG. 9A. As can be seen, at this pressure the cuff retained its tubular shape. The cuff was subsequently further inflated with a second quantity of ambient-pressure air that resulted in a pressure greater than the local maximum pressure $P_{MAX}$ (the second quantity of ambient-pressure air bringing the total cuff volume to be 2.23 * V1 and the second pressure was 30.1 cm H2O), resulting in the cuff shape shown in FIG. 9B. As the cuff was inflated toward the second pressure, the cuff pressure first rose to the local maximum pressure $P_{MAX}$ at 37.1 cm H2O at an inflation volume of 2.04 * V1; thereafter, the cuff began to gradually deform by developing a localized bulge on one side of the cuff, until the cuff formed a prominent bulge deformation 320 to accommodate the extra quantity of air. As illustrated in FIGS. 9B, 9C, and 9D, the bulge formed on the right side of the cuff, such that the cuff right side cross-section IXD-IXD had an area S2 that was significantly greater (at least 20% greater) than the parallel left side cross-section IXC-IXC area S1. Bulge deformation 320 started to occur in the volume region immediately to the right of the local maximum pressure $P_{MAX}$, as labeled in FIG. 6. A special characteristic of the bulge formation, compared to before the bulge formation, is the following: during inflation prior to the bulge formation (i.e., before arriving at the local maximum pressure $P_{MAX}$), the areas S1 and S2 of both cross-sections IXC-IXC and IXD-IXD increase with increase in total volume. In contrast, during inflation after the bulge formation (i.e., at volumes greater than the volume at the local maximum pressure $P_{MAX}$), the cross-sectional area S1 actually decreases, while the cross-sectional area S2 increases with the increase of total inflation volume between the volume at the local maximum pressure $P_{MAX}$ and the volume of 2.5 * V1.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A laryngeal mask airway (LMA) device comprising:
    a single-layer inflatable annular cuff, which is insertable through a mouth of a patient to an inserted location within the patient, such that an anterior side of the cuff forms a seal around a laryngeal inlet of the patient upon inflation of the cuff;
    a backplate attached to the cuff; and
    an airway tube having (a) a proximal end that is configured to be disposed outside the patient's mouth when the cuff is at the inserted location, and (b) a distal end that is in fluid communication with a port of the backplate, wherein the port is open through a hollow center of the annular cuff,
    wherein the cuff, when disposed in free space, is characterized by a pressure-volume curve that represents the pressure in the cuff when inflated to different volumes of the cuff that include a low-pressure volume corresponding to a low pressure of 10 cm H2O, wherein the pressure-volume curve includes:
        a local maximum pressure at a medium volume of the cuff between 1.25 and 2.4 times the low-pressure volume, wherein the local maximum pressure is between 15 and 120 cm H2O, and
        respective high-volume medium pressures corresponding to all high volumes of the cuff that are between 2.5 and 3 times the low-pressure volume, wherein each of the high-volume medium pressures is between 15 cm H2O and 99% of the local maximum pressure.

2. The LMA device according to claim 1, wherein each of the high-volume medium pressures is less than 95% of the local maximum pressure.

3. The LMA device according to claim 1, wherein each of the high-volume medium pressures is less than 90% of the local maximum pressure.

4. The LMA device according to claim 1, wherein the local maximum pressure is less than 60 cm H2O.

5. The LMA device according to claim 4, wherein the local maximum pressure is less than 40 cm H2O.

6. The LMA device according to claim 1, wherein the local maximum pressure is greater than 20 cm H2O.

7. The LMA device according to claim 1, wherein the pressure-volume curve has the local maximum pressure at a medium volume that is between 1.5 and 2.2 times the low-pressure volume.

8. The LMA device according to claim 1, wherein the cuff is configured such that when disposed in free space and inflated to the low-pressure volume of the cuff, further inflation of the cuff with an incremental quantity of air results in a medium pressure in the cuff that is less than 30 cm H2O, the incremental quantity of air having a volume, when the air is at ambient pressure, equal to 10% of the low-pressure volume of the cuff.

9. The LMA device according to claim 1, wherein the cuff is configured such that when disposed in free space and inflated to the low-pressure volume of the cuff, further inflation of the cuff with an incremental quantity of air results in a medium pressure in the cuff that is less than 60 cm H2O, the incremental quantity of air having a volume, when the air is at ambient pressure, equal to 20% of the low-pressure volume of the cuff.

10. The LMA device according to claim 1,
    wherein the cuff is configured such that when disposed in free space and inflated to one of the high volumes of the cuff corresponding to a first pressure in the cuff, further inflation of the cuff with an incremental quantity of air results in a second pressure in the cuff that is less than the first pressure, and wherein the incremental quantity of air has a volume, when the air is at ambient pressure, equal to 10% of the one of the high volumes of the cuff.

11. The LMA device according to claim 1,
wherein the cuff is configured such that when disposed in free space and inflated to one of the high volumes of the cuff corresponding to a first pressure in the cuff, further inflation of the cuff with an incremental quantity of air results in a second pressure in the cuff that is less than the first pressure, and wherein the incremental quantity of air has a volume, when the air is at ambient pressure, equal to 30% of the one of the high volumes of the cuff.

12. The LMA device according to claim 1, wherein the cuff comprises non-latex synthetic polyisoprene.

13. The LMA device according to claim 12, wherein the cuff comprises primarily non-latex synthetic polyisoprene by weight.

14. The LMA device according to claim 1, wherein the thickness of a wall of the cuff is between 0.05 mm and 0.5 mm at the thinnest of non-attached locations of the cuff that are not attached to the backplate.

15. The LMA device according to claim 14, wherein the thickness of the cuff wall is between 0.05 mm and 0.3 mm at the thinnest of the non-attached locations.

16. The LMA device according to claim 1, wherein the cuff, when disposed in free space and inflated to the low-pressure volume of the cuff, has an asymmetric toroidal tubular shape.

17. The LMA device according to claim 16, wherein the cuff, when disposed in free space and inflated to the low-pressure volume of the cuff, has an average low-pressure external cross-sectional area, measured perpendicular to the center line of the cuff, that is less than 225 mm2.

18. The LMA device according to claim 17, wherein the average low-pressure external cross-sectional area is less than 81 mm2.

19. A method comprising:
inserting a single-layer inflatable annular cuff of a laryngeal mask airway (LMA) device through a mouth of a patient to an inserted location within the patient, such that a proximal end of an airway tube of the LMA device is disposed outside the patient's mouth, and a distal end of the airway tube is in fluid communication with a port of a backplate of the LMA device attached to the annular cuff, wherein the port is open through a hollow center of the annular cuff; and inflating the cuff such that an anterior side of the cuff forms a seal around a laryngeal inlet of the patient, wherein the cuff, when disposed in free space, is characterized by a pressure-volume curve that represents the pressure in the cuff when inflated to different volumes of the cuff that include a low-pressure volume corresponding to a low pressure of 10 cm H2O, wherein the pressure-volume curve includes:

a local maximum pressure at a medium volume of the cuff between 1.25 and 2.4 times the low-pressure volume, wherein the local maximum pressure is between 15 and 120 cm H2O, and respective high-volume medium pressures corresponding to all high volumes of the cuff that are between 2.5 and 3 times the low-pressure volume, wherein each of the high-volume medium pressures is between 15 cm H2O and 99% of the local maximum pressure.

20. The method according to claim 19, wherein each of the high-volume medium pressures is less than 95% of the local maximum pressure.

21. The method according to claim 19, wherein the local maximum pressure is less than 60 cm H2O.

22. The method according to claim 19, wherein the local maximum pressure is greater than 20 cm H2O.

23. The method according to claim 19, wherein the pressure-volume curve has the local maximum pressure at a medium volume that is between 1.5 and 2.2 times the low-pressure volume.

24. The method according to claim 19, wherein the cuff is configured such that when disposed in free space and inflated to the low-pressure volume of the cuff, further inflation of the cuff with an incremental quantity of air results in a medium pressure in the cuff that is less than 60 cm H2O, the incremental quantity of air having a volume, when the air is at ambient pressure, equal to 20% of the low-pressure volume of the cuff.

25. The method according to claim 19,
wherein the cuff is configured such that when disposed in free space and inflated to one of the high volumes of the cuff corresponding to a first pressure in the cuff, further inflation of the cuff with an incremental quantity of air results in a second pressure in the cuff that is less than the first pressure, and wherein the incremental quantity of air has a volume, when the air is at ambient pressure, equal to 10% of the one of the high volumes of the cuff.

26. The method according to claim 19, wherein the cuff comprises non-latex synthetic polyisoprene.

27. The method according to claim 26, wherein the cuff comprises primarily non-latex synthetic polyisoprene by weight.

28. The method according to claim 19, wherein the thickness of a wall of the cuff is between 0.05 mm and 0.5 mm at the thinnest of non-attached locations of the cuff that are not attached to the backplate.

29. The method according to claim 19, wherein the cuff, when disposed in free space and inflated to the low-pressure volume of the cuff, has an asymmetric toroidal tubular shape.

30. The method according to claim 29, wherein the cuff, when disposed in free space and inflated to the low-pressure volume of the cuff, has an average low-pressure external cross-sectional area, measured perpendicular to the center line of the cuff, that is less than 225 mm2.

* * * * *